United States Patent [19]

Mrozik

[11] Patent Number: 4,874,749

[45] Date of Patent: * Oct. 17, 1989

[54] 4"-DEOXY-4-N-METHYLAMINO AVERMECTIN BLA/BLB

[75] Inventor: Helmut Mrozik, Matawan, N.J.

[73] Assignee: Merck & Co., Inc., Rahway, N.J.

[*] Notice: The portion of the term of this patent subsequent to Jan. 24, 2001 has been disclaimed.

[21] Appl. No.: 80,942

[22] Filed: Jul. 31, 1987

[51] Int. Cl.$^4$ .................. A61K 31/70; C07H 17/04
[52] U.S. Cl. ............................ 514/30; 536/7.1; 71/88
[58] Field of Search ............... 536/7.1; 514/27, 30; 71/88

[56] References Cited

U.S. PATENT DOCUMENTS 4,427,663 1/1984 Mrozik ........................... 536/7.1

Primary Examiner—Amelia Burgess Yarbrough
Assistant Examiner—Elli Peselev
Attorney, Agent, or Firm—David L. Rose; Hesna J. Pfeiffer; Michael C. Sudol

[57] ABSTRACT

The compound 4"-deoxy-4"-N-methylamino avermectin Bla/Blb has been discovered to have unexpected properties when used as an agricultural insecticide. Specifically, the compound is considerably more active against insects, particularly lepidoptera, than closely related compounds, and the compound exhibits significantly lower levels of mammalian toxicity and aquatic animal toxicity. Thus the compound presents a much wider margin of safety towards the human appliers of the compound and to other mammals that come in contact with treated areas as well as wider margins of safety to aquatic animals to which any spray drift or run-off containing the compound may be directed.

7 Claims, No Drawings

4"-DEOXY-4-N-METHYLAMINO AVERMECTIN B1A/B1B

BACKGROUND OF THE INVENTION

U.S. Pat. No. 4,427,663 to Mrozik describes the use of certain 4"-deoxy-4"-amino derivatives of avermectin compounds, including N-alkyl derivatives. The compounds are described as being anthelmintics and agricultural insecticides. It has been surprisingly discovered that 4"-deoxy-4"-N-methylamino avermectin B1a/B1b has a significantly higher level of activity and lower level of mammalian and aquatic life toxicity when compared to other 4"-amino compounds and other related avermectin compounds.

SUMMARY OF THE INVENTION

This invention is related to a novel compound which has been found to have surprisingly high levels of activity and low levels of toxicity when used as an agricultural insecticide. The compound is 4"-deoxy-4"-N-methyl amino avermectin B1a/B1b, and it is an object of this invention to describe such compound. It is a further object of this invention to describe the preparation and use of such compound as an agricultural insecticide. A still further object is to describe the unexpectedly high levels of activity, the unexpectedly low levels of toxicity and the resultant very wide safety margin of such compound. Other objects of this invention are to describe compositions containing such compound intended for use as an agricultural insecticide and still other objects will become apparent from a reading to the following disclosure.

DISCLOSURE OF THE INVENTION

The compound, or more exactly the mixture of compounds named as 4"-deoxy-4"-N-methylamino avermectin B1a/B1b is best described in the following structural formula:

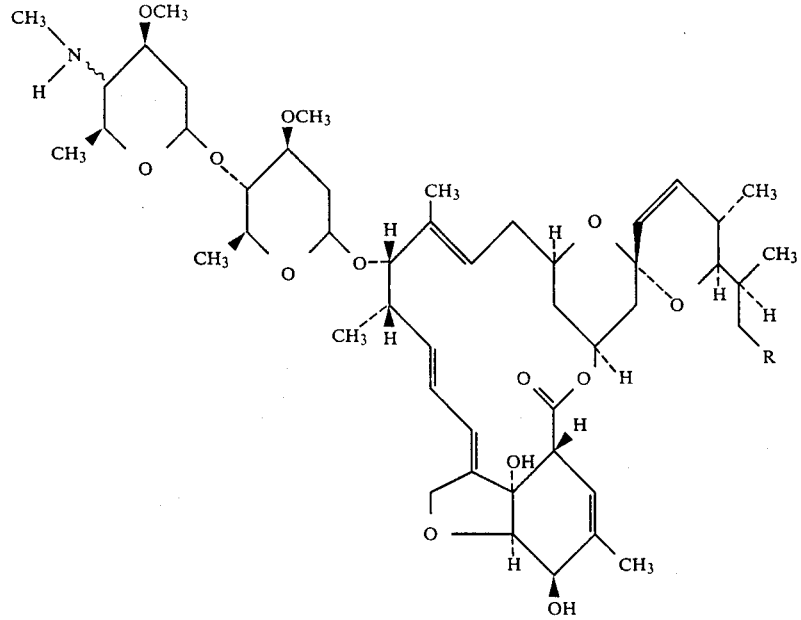

wherein R is hydrogen or methyl.

When R is a methyl group, the compound is 4"-deoxy-4"-N-methylamino avermectin B1a and when R is hydrogen, the compound is 4"-deoxy-4"-N-methylamino avermectin B1b.

The pharmaceutically acceptable acid addition salts of the foregoing compounds are also included within the ambit of the instant invention. In particular the mineral acid salts such as the hydrochloride, nitrate, sulfate phosphate and the like and organic acids such as the tartarate, maleate and the like.

Generally the instant compound is used as a mixture of the two compounds since the structural differences are very slight, amounting to the difference between a sec-butyl group and an isopropyl group, and the two compounds have substantially the same chemical reactivity and biological activities. Reference in the instant application is used to either the "compound" or "compounds", and this is intended to include either the mixture of the B1a and B1b compounds, or the individual B1a and B1b compounds. For convenience, the nomenclature B1a/B1b is employed to indicate the individual compounds and the mixture of such compounds.

The above compound exists in two stereochemical forms where the N-methyl group is below the plane of the ring ($\alpha$) or above the plane of the ring ($\beta$). During the preparation of the compound the $\beta$-compound is prepared in greater abundance than the $\alpha$-compound. In testing both compounds however, they are observed to have substantially the same activity.

The instant compound is prepared from avermectin B1a/B1b which is a compound with a hydroxy group at the 4" position. This compound is oxidized to the ketone which, in turn is reductively aminated with N-methyl amine to form the 4"-deoxy-4"-N-methylamino group. During the process the $\alpha$-configuration of the original hydroxy group is significantly inverted to the $\beta$-position which thus results in the 4"-deoxy-4"-N-methylamino substituent being obtained in less quantity than the major product 4"-deoxy-4"-epi-N-methylamino avermectin B1a/B1b. The reaction is illustrated in the following reaction scheme wherein only the terminal a-L-oleandrosyl molecular group is shown.

The remainder of the molecule is unchanged and is as shown in Structure I.

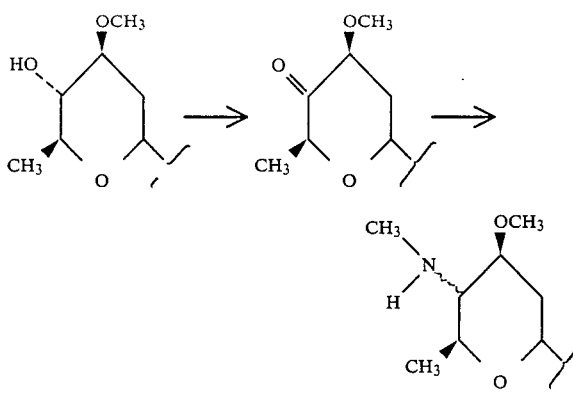

In the first step of the above reaction scheme, avermectin Bla/Blb is oxidized to the 4″-keto compound. During the procedure the 5-hydroxy group should be protected to prevent multiple reactions. The preferred protecting group is the t-butyl dimethylsilyl group. In the oxidation of the 5-O-protected avermectin Bla/Blb using oxalyl chloride, trifluoroacetic anhydride in dimethylsulfoxide, N-chlorosuccinimide in dimethyl sulfide, and the like may be employed. The reaction is generally carried out in as inert solvent such as methylene chloride from $-50°$ to $-80°$ C. and is generally complete in less than 2 hours. The product is isolated using known techniques. In the next step the 4″-keto compound is aminated with N-methyl ammonium salts, preferably N-methyl ammonium acetate, to form the 4″-N-methyamino substituent. The reaction is carried out at about $-25°$ to $+10°$ C. in an inert solvent such as a lower alkanol. The N-methyl ammonium salt complex is reduced using, for example sodium cyanoborohydride to form the 4″-deoxy-4″-N-methyl amino compound. The compound is isolated using techniques known to those skilled in the art.

It has been discovered that the above-named 4″-deoxy-4″-N-methylamino avermectin Bla/Blb compound is surprisingly active against agricultural pests such as lepidopterous insects, in particular *Heliothis spp., Spodoptera spp, Trichoplusia Ni,* and the like, and surprisingly less toxic than closely related compounds against beneficial animals likely to come in contact with the compound such as aquatic organisms including micro crustaceans such as *Daphnia magna* and fish such as sunfish and trout. This results in a highly increased margin of safety since smaller amounts of a less toxic compound are used.

For example, tests have been carried out in which the instant compound was compared with avermectin Bla/Blb (avermectin the starting material for the instant compound) and 4″-deoxy-4″-amino avermectin Bla/Blb. In an LD$_{90}$ test (Lethal Dose for 90% of the insects) against southern armyworm and tobacco budworm, avermectin Bla/Blb required >34.0 and >1.3 micrograms/GWT (Gram Weight of the Test insect) respectively; 4″-deoxy 4″-amino avermectin Bla/Blb required 3.4 and 1.3 micrograms/GWT respectively; and 4″-deoxy-4″-epi-N-methylamino avermectin Bla/Blb requires 0.542 and 0.4 micrograms/GWT respectively. Expressed another way, 4″-deoxy-4″-amino avermectin Bla/Blb was 60% effective at 0.5 micrograms/GWT against southern armyworm while 4″-deoxy-4″-epi-N-methylamino avermectin Bla/Blb was 90% effective at 0.125 micrograms/GWT against the same parasite.

With respect to the relative safety of the instant compound, it will be appreciated that when chemical compounds are used as agricultural sprays, one major concern is the effect such compounds have on lakes, streams and other aquatic environments, and the animals that inhabit them since very often pesticides find their way into aquatic areas from rain, irrigation run-off or spray drift from treated fields.

At the lower end of the aquatic food chain is the minute crustacean *Daphnia magna* which is very susceptible to chemical pesticides and, when adversely affected by such pesticides, has severe deleterious effects on the higher aquatic life which uses Daphnia as a primary food source. In particular, many avermectin compounds are known to be highly toxic to Daphnia.

In one test of the instant compound (see Example 5) and closely related avermectin compounds against *Daphnia magna,* described as a 48 hour LC$_{50}$ test, that is, the concentration of compound which is fatal to 50% of *Daphnia magna* over a 48 hour period, it was observed that avermectin Bla/Blb has an LC$_{50}$ of 300 ppt (parts per trillion); and 4″-deoxy-4″-amino avermectin Bla/Blb has an LC$_{50}$ of 600 ppt. This is to be compared with 4″-deoxy-4″-epi-N-methylamino avermectin Bla/Blb which had an LC$_{50}$ at 2900 ppt, that is, the instant compound in almost 5 times less toxic against this important aquatic food source then the 4″-amino compound and almost 10 times less toxic than the avermectin Bla/Blb compound.

The instant compound of this invention is also useful as an animal health antiparasitic agent, in particular as an anthelmintic agent, ectoparasiticidal agent, acaricide and insecticide. See the above cited patent by Mrozik.

The observed increases in activity against lepidopterous insects and decreases in toxicity results in an expansion of the safety factor of the instant compound many times that previously observed.

The following examples are provided in order that the invention might be more fully understood. The examples are not to be construed as limitations upon the scope of the invention.

EXAMPLE 1

5-O-t-Butyldimethylsilylavermectin Bla/Blb

A solution of 50 g. of avermectin in Bla/Blb (dried over P$_2$O$_5$ in high vacuum to constant weight), 24 g of imidazole and 24 g of tert-butyldimethylsilyl chloride in 400 ml of anhydrous N,N-dimethylformamide was stirred at room temperature for 50 minutes. The reaction mixture was poured into 1.5 l of ice cold water and the aqueous phase was extracted four times with 200 ml of ether. The organic phase was washed twice with water, aqueous sodium chloride solution, dried with magnesium sulfate and concentrated in vacuo to a white foam. The crude product was purified by silica gel column chromatography with a methylene chloride-ethyl acetate-90:10 to 70:30 solvent system to give 46.5 g of 5-O-t-butyldimethylsilylavermectin Bla/Blb as an amorphous foam, which was characterized by its $^1$H-NMR- and mass spectra.

EXAMPLE 2

5-O-t-Butyldimethylsilyl-4"-oxoavermectin B1a/B1b

To a solution containing 9.1 ml of oxalyl chloride in 230 ml of dry methylene chloride stirred at −60° C. was added 15 ml of dry dimethylsulfoxide dissolved in 120 ml of dry methylene chloride during 15 min. Then a solution of 46.5 g of 5-O-t-butyldimethylsilylavermectin B1a/B1b dissolved in 230 ml of dry methylene chloride was added over a period of 15 minutes while maintaining the temperature at −60° C. The reaction mixture was stirred at this temperature for 30 minutes when 65 ml of dry triethylamine was added. The mixture was stirred for 5 additional minutes at −60° C., the cooling bath was removed and the reaction mixture was allowed to come to ambient temperature. After addition of water the reaction product was extracted with methylene chloride, the extract was washed with water, dried and concentrated in vacuo to 45.5 g of a yellow foam. This was identified by its mass and NMR spectra as 5-O-t-butyldimethylsilyl-4"-oxoavermectin B1a/B1b, which was used for further chemical reactions without purification.

EXAMPLE 3

4"-Deoxy-4"-epi-methylamino-5-O-t-butyldimethyl-silylavermectin B1a/B1b and 4"-deoxy-4"-methylamino-5

A solution of 26 ml of glacial acetic acid in 300 ml of methanol was treated with methylamine gas at 0° C. until the pH of the solution reached 9.0. To this a solution containing 44.5 g of 5-O-t-butyldimethylsilyl-4"-oxoavermectin B1a/B1b in 200 ml of methanol was added, and the reaction mixture was stirred at room temperature for 1 hour, when a solution of 3.5 g of sodium cyanoborohydride in 75 ml of methanol was added dropwise over 10 minutes. After 50 minutes the reaction mixture was poured into 1.5 l of cold aqueous sodium carbonate solution and the product was extracted with ether. The extract was washed with water, dried, and concentrated in vacuo to 44.8 g of yellow foam. Thin layer chromatography (silica gel, ethyl acetate 85:15) of the crude product at this point shows several spots. Further purification by silica gel column chromatography using ethyl acetate solvent mixtures gave 4.7 g of 5-O-t-butyldimethylsilyl-4"-epiavermectin B1a/B1b, 1.2 g of 4"-deoxy-N-methylamino-5-O-t-butyldimethylsilyl-avermectin B1a/B1b, and 14 g of 4"-deoxy-4"-epi-N-methylamino-5-O-t-butyldimethylsilyl-avermectin B1a/B1b as light foams, which were characterized by their mass spectrum and their $^1H$-, and $^{13}C$-NMR spectra.

EXAMPLE 4

4"-Deoxy-4"-epi-methylaminoavermectin B1a/B1b

A solution of 14 g of 4"-deoxy-4"-epi-methylamino-5-O-t-butyldimethylsilylavermectin B1a/B1b in 200 ml of methylene chloride and a solution of 7 g of p-toluenesulfonic acid monohydrate in 500 ml of methylene chloride was mixed and stirred at room temperature for 45 minutes, and then poured into dilute aqueous sodium carbonate solution. The product was extracted with EtOAc, washed with water and dried over magnesium sulfate, concentrated in vacuo, and purified by preparative silica gel column chromatography with a methylene chloride-methanol 95:5 solvent mixture to give 6.7 g of 4"-deoxy-4"-epimethylaminoavermectin B1a/B1b, which was identified by NMR and mass spectra.

Following the above procedures using as starting material the compound 4"-deoxy-N-methylamino-5-O-t-butyldimethylsilyl-avermectin B1a/B1b there is obtained 4"-deoxy-N-methylaminoavermectin B1a/B1b.

EXAMPLE 5

The insect toxicity of 4"-deoxy-4"-epi-N-methylaminoavermectin B1a/B1b is demonstrated in the following tests.

In a foliar ingestion toxicity study against *Spodoptera eridania* larvae 4"-deoxy-4"-epimethylamino avermectin B1a/B1b was 1166 times more toxic than avermectin B1a/B1b as measured by an $LC_{90}$ test (lethal concentration for 90% of the insects). The $LC_{90}$ value for 4"-deoxy-4"-epimethylamino avermectin B1a/B1b was 0.005 ppm versus 5.83 ppm for avermectin B1a/B1b.

In a foliar ingestion toxicity study against *Heliothis virescens* larvae 4"-deoxy-4"-epimethylamino avermectin B1a/B1b was 43 times more toxic than avermectin B1a/B1b was 43 times more toxic than overmectin B1a/B1b as measured by an $LC_{90}$ test. The $LC_{90}$ value for 4"-deoxy-4"-epimethylamino avermectin B1a/B1b was 0.003 ppm versus 0.128 ppm for avermectin B1a/B1b.

In a foliar ingestion toxicity against *Heliothis zea* larvae 4"-deoxy-4"-epimethylamino avermectin B1a/B1b was 105 times more toxic than avermectin B1a/B1b as measured by an $LC_{90}$ test. The $LC_{90}$ value for 4"-deoxy-4"-epimethylamino avermectin B1a/B1b was 0.002 ppm versus 0.21 ppm for avermectin B1a/B1b.

In a contact toxicity study against *Spodoptera eridania* larvae 4"-deoxy-4"-epimethylamino avermectin B1a/B1b was 4.times more toxic than 4"-deoxy-4"-epiamino avermectin B1a/B1b as measured at 96 hours in microgram per gram body weight. (BTI 159).

In a contact toxicity study against *Heliothis virescens* larvae 100% mortality at 0.4 microgram/g body weight and 25% mortality at 0.1 microgram/g body weight was observed with 4"-deoxy-4"-epimethylamino avermectin B1a/B1b versus 30% mortality and 5% mortality at these doses with 4"-deoxy-4"-epiamino avermectin B1a/B1b.

In a contact toxicity study against *Heliothis zea* larvae 100% mortality was observed at 96 hours with 4.0 mircrogram/gram body weight, 100% mortality at 0.4 microgram/g body weight and 20% mortality at 0.04 microgram/gram body weight with 4"-deoxy-4"-epimethylamino avermectin B1a/B1b. In the same study 100% mortality was observed at 4.0 microgram per gram body weight, 90% at 0.4 microgram per gram body weight and 0% at 0.04 microgram per gram body weight with 4"-deoxy-4"-epiamino avermectin B1a/B1b.

EXAMPLE 6

Acute Toxicity to Daphnia magna

Ten *Dahpnia magna* (first instar less than 24 hours old) were placed in a 250 ml glass beaker containing 200 ml of an aqueous solution of the test compounds in concentrations from 1.0 to 10 microgram/liter (ppb). The test compounds were dissolved in a small volume of acetone for dilution with water. The solvent control contained 0.010 ml of acetone which is equivalent to the highest test concentration. A control and solvent control was added to the experiment which was conducted in two replicates. All concentrations were observed once at 24 and 48 hours for mortality and abnormal effects such as surfacing, clumping of the daphnids together and daphnids lying on the bottom of the beakers.

TABLE 1

Mortality Rates of Daphnia magna to aqueous solutions of 4"-Deoxy-4"-epi-N—methylaminoavermectin B1a/B1b.

| Nominal Concentration | Percent Mortality | |
|---|---|---|
| microgram/l | 24 hr | 48 hr |
| Control | 0 | 0 |
| Solvent Control | 0 | 0 |
| 1.0 | 0 | 0 |
| 1.8 | 0 | 5 |
| 3.2 | 20 | 70 |
| 5.6 | 30 | 95 |
| 10.0 | 90 | 100 |

TABLE 2

Acute Toxicity to Daphnia magna

| Compound | $LC_{50}$ (micrograms/l) 48 hours |
|---|---|
| 4"-deoxy-4"-epi-N—methylamino avermectin B1a/B1b | 2.9 |
| 4"-deoxy-4"-aminoavermectin B1a/B1b | 0.6 |
| avermectin B1a/B1b | 0.34 |

EXAMPLE 7

Acute Toxicity to Rainbow Trout (Salmo gairdneri)

The static fish bioassay was conducted in five gallon glass vessels containing 15 liters of soft reconstituted water composed of the following compounds in the amounts stated per liter of deionized water:

48 mg $NaHCO_3$
30 mg $CaSO_4"2 H_2O$
30 mg $MgSO_4$
2 mg KCl

This reconstituted water was prepared to yield a total hardness of 40–48 mg/l as $CaCO_3$, a total alkalinity of 20–30 mg/l as $CaCO_3$ and an initial pH of 7.2 to 7.6. The 0-hour measured control water parameters of this dilution water were dissolved oxygen 9.7 mg/l and pH 7.4.

The test vessels were kept in a water bath at 12° C. The test fish were acclimated to the dilution water and test temperature and held without food for 48–96 hours prior to testing.

Based on the results of preliminary testing, six concentrations of the test compound with ten fish per concentration were selected for the definitive bioassay. The definitive test concentrations were obtained by transferring appropriate aliquots of a working standard directly to the test chambers. The working standard was prepared in dimethylformamide (DMF). Also included was a dilution water control and a solvent control chamber.

The fish were added to the test chambers by random assignment within 30 minutes after addition of test material. All test organisms were observed once every 24 hours for mortality and abnormal (sub-lethal) effects. any dead individuals were removed from the test chambers after each 24-hour observation. The $LC_{50}$ statistic and its 95 percent confidence limits were calculated by employing a computerized standard program.

TABLE 3

Mortality Rates of Rainbow Trout (Salmo gairdneri) to aqueous solutions of 4"-Deoxy-4"-epi-N—methylaminoavermectin B1a/B1b

| Nominal Concentration | Percent Mortality | | |
|---|---|---|---|
| (mg/l) | 24 hr | 48 hr | 96 hr |
| Control | 0 | 0 | 0 |
| Solvent Control | 0 | 0 | 0 |
| 0.056 | 0 | 0 | 0 |
| 0.10 | 0 | 0 | 0 |
| 0.18 | 0 | 0 | 0 |
| 0.32 | 0 | 0 | 0 |
| 0.56 | 0 | 0 | 20 |
| 1.0 | 0 | 0 | 100 |

TABLE 4

Acute Toxicity to Rainbow Trout (Salmo gairdneri)

| | $LC_{50}$ in milligrams/liter (ppm) | | |
|---|---|---|---|
| Compound | 24 | 48 | 96 hours |
| 4"-deoxy-4"-epi-N—methylamino avermectin B1a/B1b | >1.0 | >1.0 | 0.67 |
| avermectin B1a/B1b | >0.006 | 0.0046 | 0.0032 |

EXAMPLE 8

Acute Toxicity to Bluegill Sunfish (Lepomis macrochirus)

The same test procedure was used as described in example 6, except that Bluegill Sunfish were used and that the test vessels were kept in a water bath at 22° C.

TABLE 5

Mortality Rates of Bluegill Sunfish (Lepomis macrochirus) to aqueous solutions of 4"-Deoxy-4"-epi-N—methylaminoavermectin B1a/B1b

| Nominal Concentration | Percent Mortality | | |
|---|---|---|---|
| (mg/l) | 24 hr | 48 hr | 96 hr |
| Control | 0 | 0 | 0 |
| Solvent Control | 0 | 0 | 0 |
| 0.056 | 0 | 0 | 0 |
| 0.10 | 0 | 0 | 0 |
| 0.18 | 0 | 0 | 0 |
| 0.32 | 0 | 0 | 100 |
| 0.56 | 0 | 90 | 100 |
| 1.0 | 100 | 100 | 100 |

TABLE 6

Acute Toxicity to Bluegill Sunfish (Lepomis macrochirus)

| | $LC_{50}$ in milligrams/liter (ppm) | | |
|---|---|---|---|
| Compound | 24 | 48 | 96 hours |
| 4"-deoxy-4"-epi-N—methylamino avermectin B1a/B1b | 0.75 | 0.45 | 0.24 |
| avermectin B1a/B1b | 0.029 | 0.019 | 0.0096 |

What is claimed is:

1. 4"-Deoxy-4"-N-methylaminoavermectin B1a/B1b and pharmaceutically acceptable acid addition salts thereof.

2. A process for the preparation of the compound of claim 1 which comprises treating 5-O-t-butyl-dimethylsilyl protected 4"-oxoavermectin B1a/B1b, with $NaCNBH_3$ in the presence of an N-methyl ammonium salt.

3. A process of claim 2 wherein the N-methyl ammonium salt is an N-methyl ammonium acetate.

4. A method for the treatment of agricultural insects which comprises applying to an area infested with such agricultural insects an effective amount of the compound of claim 1.

5. The method of claim 4 wherein the agricultural insect is a lepidopterous insect.

6. A composition useful as an agricultural insecticide which comprises an inert carrier and an effective amount of the compound of claim 1.

7. A method of treating animal parasitic infections which comprises the administration of an effective amount of the compound of claim 1 to an animal in need of such treatment.

* * * * *